(12) United States Patent
Murthy (10) Patent No.: US 9,445,802 B2
(45) Date of Patent: Sep. 20, 2016

(54) OPHTHALMIC TOOL FOR EYE IMAGING DEVICE

(71) Applicant: Raghu Murthy, San Marino, CA (US)

(72) Inventor: Raghu Murthy, San Marino, CA (US)

( * ) Notice: Subject to any disclaimer, the term of this patent is extended or adjusted under 35 U.S.C. 154(b) by 0 days.

(21) Appl. No.: 14/624,857

(22) Filed: Feb. 18, 2015

(65) Prior Publication Data

US 2016/0235395 A1 Aug. 18, 2016

(51) Int. Cl.
*A61B 1/32* (2006.01)
*A61B 17/02* (2006.01)
*A61B 3/15* (2006.01)
*A61B 3/125* (2006.01)

(52) U.S. Cl.
CPC ........... *A61B 17/0231* (2013.01); *A61B 3/125* (2013.01); *A61B 3/152* (2013.01)

(58) Field of Classification Search
CPC .................................................. A61B 17/0231
USPC ........................................................... 600/236
See application file for complete search history.

*Primary Examiner* — Ellen C Hammond
*Assistant Examiner* — Stuart S Bray (57) ABSTRACT

An ophthalmic tool includes an ophthalmic speculum for holding a patient's eye open and for guiding a lens probe of an eye imaging device to be directly contacted with a cornea of the patient's eye. The ophthalmic speculum includes two eyelid distensible frames, a mechanism to spread the eyelid distensible frames apart, and a probe guiding frame including a plurality of probe guiders spacedly extended from the eyelid distensible frames. Each probe guider has a peak upwardly extended above the eyelid distensible frame that serves as a guiding point and forms a probe guiding cavity within the guiding points of the probe guiders. The lens probe is guided to be disposed within the probe guiding cavity via the guiding points before and after the lens probe is aligned and contacted with the cornea of the patient's eye in a proper upright orientation.

20 Claims, 5 Drawing Sheets

OPHTHALMIC TOOL FOR EYE IMAGING DEVICE

BACKGROUND

1. Field of the Invention

The present invention relates to an ophthalmic tool. More particularly, the present invention relates to an ophthalmic tool for an eye imaging device, wherein an ophthalmic speculum is used to hold a patient's eyelids open and to retain a lens probe of the eye imaging device in order to ensure the lens probe to be contacted with and placed on the cornea of the patient.

2. Discussion of the Related Art

Eye imaging device, especially for pediatric retinal imaging device such as "RetCam", is a device for screening retinopathy of prematurity (ROP), newborn screening examination, or other pediatric eye examination, wherein the eye imaging device is specifically for the eyes of infants and/or children to capture ophthalmic images electronically. Generally speaking, the eye imaging device comprises a hand-held lens probe placing on the cornea of the patient in an upright manner. After the optical coupling gel is applied on the eye anterior surface, the lens probe of the eye imaging device must be held properly to leave a gap filled by the optical coupling gel in order to contact with the cornea of the patient. Then, the lens probe is displaced by either a rotational or angular movement in order to capture different ophthalmic images at different angles.

An eyelid speculum is typically used for holding the patient's eyelids open to allow greater access to the anterior surface of the eyeball during image capturing procedure. The eyelid speculum generally comprises two engaging members adapted for insertion under upper and lower eyelids of the patient, and a frame between the two engaging members that permits relative displacement of the engaging members. A major drawback of the eyelid speculum is that the eyelid speculum does not provide any relative guidance to the lens probe of the eye imaging device. In most cases, the engaging members are two small and will block the lens probe to be contacted with the cornea of the patient. As a result, the eye imaging device may not able to capture clear ophthalmic images.

Another useful tool for eye imaging device is a sclera depressor designed to better control the globe of the eye. The sclera depressor has an elongated handle and a depressor end configured selected from a group consisting of ring depressor, ball end depressor, and flat spatula depressor. The sclera depressor is used for controlling eye position by pressing against the sclera of the eye with the depressor end, so that the lens probe can be aligned with the cornea of the patient. Accordingly, the doctor has to use one hand to hold the lens probe and the other hand to hold the sclera depressor. Since the lens probe and the sclera depressor are held in an upright manner, it is difficult for the doctor to properly control the lens probe by one hand and to control the eye position by the sclera depressor by the other hand at the same time.

Therefore, the conventional eyelid speculum and sclera depressor are not designed for incorporating with the eye imaging device.

BRIEF SUMMARY OF THE INVENTION

According to the present invention, an ophthalmic tool for an eye imaging device is described. The ophthalmic tool comprises an ophthalmic speculum specifically designed to incorporate with a pediatric retinal imaging device such as "Retcam". The ophthalmic speculum comprises two eyelid distensible frames and a probe guiding frame for retaining a lens probe of the eye imaging device in position, so that the location of the lens probe can be ensured to be contacted with and placed on the cornea of the patient.

According to the present invention, the probe guiding frame comprises a plurality of probe guiders to form a probe guiding cavity that the displacement of the lens probe is restricted within the probe guiding cavity to ensure the alignment of the lens probe with the cornea of the patient.

According to one embodiment of the present invention, each probe guider has a peak upwardly extended above the eyelid distensible frame that serves as a guiding point. The probe guiding cavity is formed within the guiding points of the probe guiders to ensure the lens probe to be guided before and after the lens probe is aligned and contacted with the cornea of the patient's eye in a proper upright orientation.

According to one embodiment of the present invention, the ophthalmic speculum further comprises a mechanism for generating an expansion force to the eyelid distensible frames for spreading the eyelid distensible frames apart.

According to one embodiment of the present invention, the ophthalmic tool further comprises an eye manipulator for moving the eyeball of the patient in order to ensure the lens probe to be aligned with the cornea of the patient. The eye manipulator has an angled arm between a manipulating end and a handle for enabling the manipulating end of the eye manipulator to be contacted with the eyeball when the lens probe is positioned in an upright manner.

The ophthalmic speculum and the eye manipulator of the present invention serve as an ophthalmic kit specifically designed to incorporate with the pediatric retinal imaging device having a hand-held lens probe.

In a preferred embodiment, each of the ophthalmic speculum and the eye manipulator is constructed of a contiguous piece of wire with a simplified structural configuration to lower the manufacturing cost thereof. With such simplified structural configuration, the ophthalmic speculum provides multiple functions of holding the patient's eye open and guiding the lens probe to be contacted with the cornea of the patient's eye in a proper upright orientation.

In a preferred embodiment, each of the ophthalmic speculum and the eye manipulator is disposable. Due to the low manufacturing and material costs, the ophthalmic speculum and the eye manipulator can be disposed for one time use for hygiene purpose.

For a more complete understanding of the present invention with its objectives and distinctive features and advantages, reference is now made to the following specification and to the accompanying drawings.

BRIEF DESCRIPTION OF THE DRAWING(S)

These and other features, aspects and advantages of the present invention will become better understood from the following description, appended claims, and accompanying figures where:

DETAILED DESCRIPTION OF THE INVENTION

Figure 1:
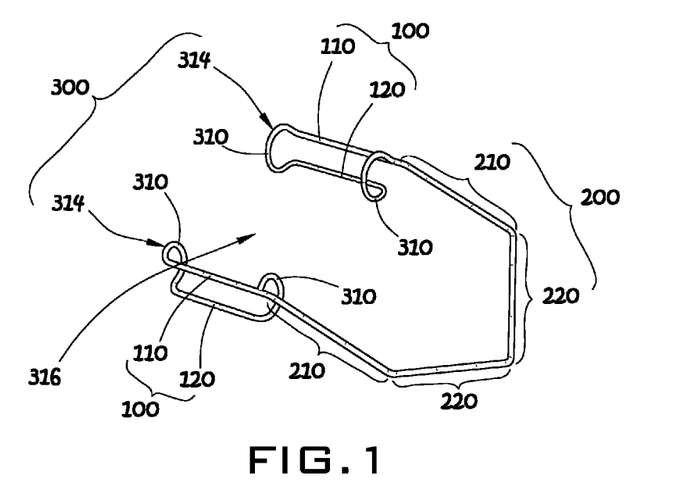
FIG. 1 is a top perspective view of an ophthalmic speculum of an ophthalmic tool according to an embodiment of the present invention, showing a lens probe disposed within a probe guiding cavity of the ophthalmic speculum.

For purposes of description herein the terms "upper," "lower," "right," "left," "rear," "front," "vertical," "horizontal" and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As used in this disclosure, the term "comprise" and variations of the term, such as "comprising" and "comprises," are not intended to exclude other additives, components, integers or steps.

The present invention provides an ophthalmic tool for incorporating with an eye imaging device with a handheld lens probe, such as the "RetCam" system, according to an embodiment is disclosed. The ophthalmic tool comprises an ophthalmic speculum and an eye manipulator to form an ophthalmic kit. The ophthalmic speculum is used for holding the patient's eye open and guiding the lens probe of the eye imaging device to be contacted with the cornea of the patient's eye in a proper upright orientation. The conventional ophthalmic speculum can only hold the patient's eye open for eye examination or eye surgery but cannot provide any guidance for the lens probe to be correctly contacted with the cornea of the patient's eye. In general, after the patient, such as an infant or a child, lies down, the patient's eye must be kept open in order to apply an optical coupling gel on the eye anterior surface. Then, the lens probe of the eye imaging device must be held properly in an upright manner to contact with the cornea of the patient for eye image capturing.

Reference is now made to certain specific non-limiting embodiment as shown in Figures. FIG. 1 depicts the ophthalmic speculum comprising two eyelid distensible frames 100, a mechanism 200 to spread the eyelid distensible frames 100 apart, and a probe guiding frame 300.

The two eyelid distensible frames 100 are adapted for engaging with an upper eyelid and a lower eyelid of the patient respectively, wherein at least a portion of each of the eyelid distensible frames 100 is arranged for insertion under the patient's eyelid.

Each of the eyelid distensible frames 100 comprises an upper distensible arm 110 and a lower distensible arm 120. The lower distensible arms 120 are arranged for insertion under the upper eyelid and the lower eyelid of the patient respectively and the upper distensible arms 110 are located above the upper eyelid and the lower eyelid of the patient respectively.

Each of the upper distensible arm 110 and the lower distensible arm 120 has a proximal end and a distal end. It is preferred that the two upper distensible arms 110 are two straight and elongated arms and parallel with each other. The two lower distensible arms 120 are also two straight and elongated arms and parallel with each other. The length of the upper distensible arm 110 between the proximal end and the distal end thereof matches with the length of the lower distensible arm 110 between the proximal end and the distal end thereof. It is preferred that a distance between the two upper distensible arms 110 matches with a distance between the two lower distensible arm 120.

The mechanism 200 is extended from the eyelid distensible frames 100 to spread the eyelid distensible frames 100 apart for holding the eye of the patient open. In FIG. 1, the mechanism 200 comprises a V-shaped wire spring integrally extended from the proximal ends of the upper distensible arms 110 to generate an expansion force along the upper distensible arms 110.

The wire spring of the mechanism 200 has two ends integrally extended from the proximal ends of the upper distensible arms 110, so that the wire spring of the mechanism 200 permits relative displacement of the upper distensible arms 110 to spread the eyelid distensible frames 100 apart. It is preferred that the wire spring of the mechanism 200 is made of shape-memory material. It is appreciated that the ends of the wire spring of the mechanism 200 can be an individual spring structure to connect with the proximal ends of the upper distensible arms 110 as known in the art.

The wire spring of the mechanism 200 is inclined with respect to the eyelid distensible frames 100, wherein the wire spring of the mechanism 200 has a first inclined portion 210 integrally extended the upper distensible arm 110 and a second inclined portion 220 integrally extended from the first inclined portion 210.

The probe guiding frame 300 is integrally extended from each of the eyelid distensible frames 100, wherein the probe guiding frame 300 not only connects the upper distensible arms 110 with the lower distensible arms 120, but also forms a guidance for the lens probe L disposing between the eyelid distensible frames 100.

The probe guiding frame 300 comprises a plurality of probe guiders 310 spacedly extended from the eyelid distensible frames 100. It is preferred that two probe guiders 310 are integrally extended from the first eyelid distensible frame 100 and another two probe guiders 310 are integrally extended from the second eyelid distensible frame 100, so that four probe guiders 310 are provided. The two probe guiders 310 at the first eyelid distensible frame 100 are aligned with the two probe guiders 310 at the second eyelid distensible frame 100. A distance between the two probe guiders 310 at the first eyelid distensible frame 100 is the same as a distance between the two probe guiders 310 at the second eyelid distensible frame 100.

Figure 2:
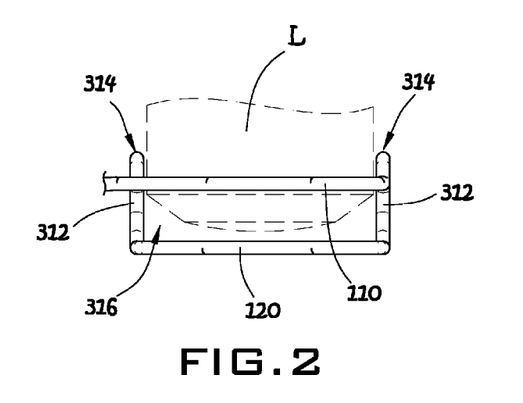
FIG. 2 is a side view of the ophthalmic speculum according to the present invention, showing the peaks of the probe guiders above the eyelid distensible frame.
Figure 3:
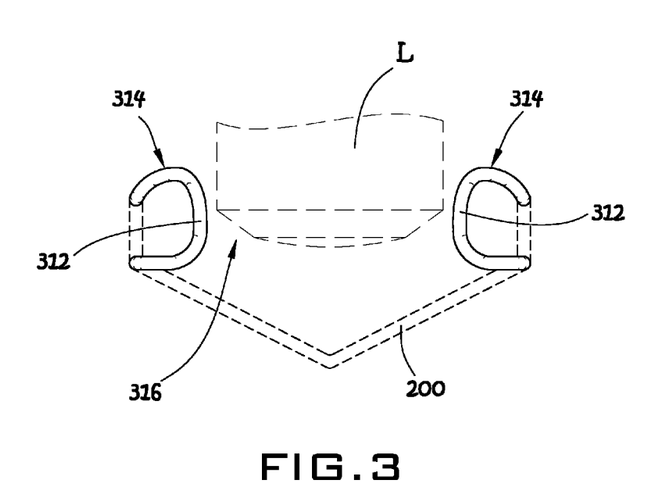
FIG. 3 is a front view of ophthalmic speculum according to the present invention, showing the curving arm extended between the upper distensible arm and the lower distensible arm.

FIGS. 2 and 3 depict that each of the probe guiders 310 comprises a curving arm 312 integrally extended between the upper distensible arm 110 and the lower distensible arm 120 of each eyelid distensible frame 100. The curving arms 312 are curved toward each other between the two eyelid distensible frames 100.

Each of the curving arms 312 has an upper end integrally extended from the upper distensible arm 110 and a lower end integrally extended from the lower distensible arm 120. Specially, the upper end and the lower end of one curving arm 312 are integrally extended from the proximal ends of the upper distensible arm 110 and the lower distensible arm 120 respectively, and the upper end and the lower end of another curving arm 312 are integrally extended from the distal ends of the upper distensible arm 110 and the lower distensible arm 120 respectively.

Each of the probe guiders 310 further has a peak 314 upwardly extended above the eyelid distensible frame 100 and serving as a guiding point, wherein a probe guiding cavity 316 is defined within the guiding points of the probe guiders 310. Therefore, the lens probe L can be disposed within the probe guiding cavity 316 before and after the lens probe L is aligned and contacted with the cornea of the patient's eye in a proper upright orientation. The depth of the probe guiding cavity 316 is defined at a distance between the peak 314 of each of the probe guiders 310 and the lower distensible arm 120. Before the lens probe L is placed to contact with the cornea of the patient's eye, the peaks 314 of the probe guiders 310 will ensure the lens probe L to be correctly disposed within the probe guiding cavity 316. After the lens probe L is disposed within the probe guiding cavity 316 to contact with the cornea of the patient's eye, the curving arms 312 will restrict any excessive movement of the lens probe L. It is worth mentioning that a size of the probe guiding cavity 316 is slightly larger than a cross sectional area of the lens probe L for allowing a slightly movement of the lens probe L within the probe guiding cavity 316. For example, a slightly rotational or angular movement of the lens probe L is allowed within the probe guiding cavity 316 for capturing different ophthalmic images at different angles.

In FIGS. 2 and 3, the peak 314 is defined at a turning point of each of the curving arms 312 between the upper end and the lower end thereof. That is to say, the curving arm 312 is curving up from the lower distensible arm 120 to extend above the upper distensible arm 110, and is then curving down to the upper distensible arm 110.

Referring again to FIGS. 2 and 3, the probe guiders 310 are extended from the eyelid distensible frames 100 in an upright manner. Therefore, the probe guiding cavity 316 is formed to have a uniform cross sectional area from the peaks 314 of the probe guiders 310. Taking four probe guiders 310 as an example, the probe guiding cavity 316 is formed to have a cubical configuration, wherein the curving arms 312 form at four corners of the probe guiding cavity 316.

Figure 4:
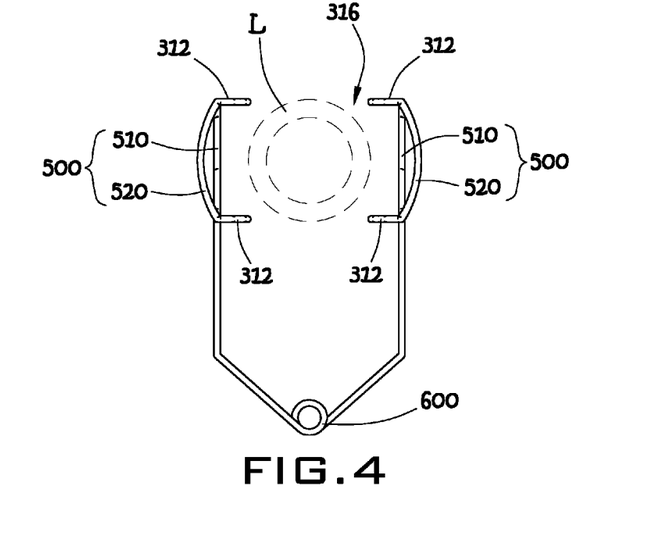
FIG. 4 shows the modification of the curved lower distensible arm and the mechanism according to the present invention.

Referring now to FIG. 4, the modification of the eyelid distensible frames 500 is shown, wherein at least one of the upper distensible arm 510 and the lower distensible arm 520 is curved. It is preferred that the two upper distensible arms 510 are two straight and elongated arms and parallel with each other and the two lower distensible arms 520 are two curving distensible arms respectively. Specifically, the two lower distensible arms 520 may have a convex shape to slip under the upper eyelid and the lower eyelid of the patient.

In FIG. 4, the modification of the mechanism 600 is also shown, wherein the vertex of the wire spring of the mechanism 600 is formed with a loop configuration to enhance the expansion force to apply along the upper distensible arms 510.

Figure 5A:
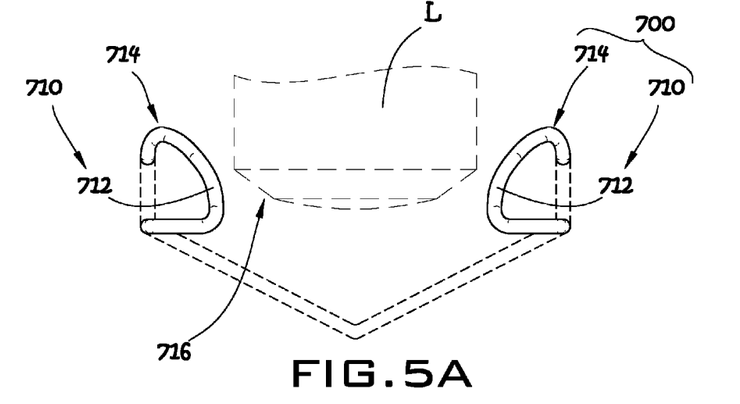
FIGS. 5A and 5B show the modification of the probe guiders extended from the eyelid distensible frames in an outward inclined manner according to the present invention.
Figure 5B:
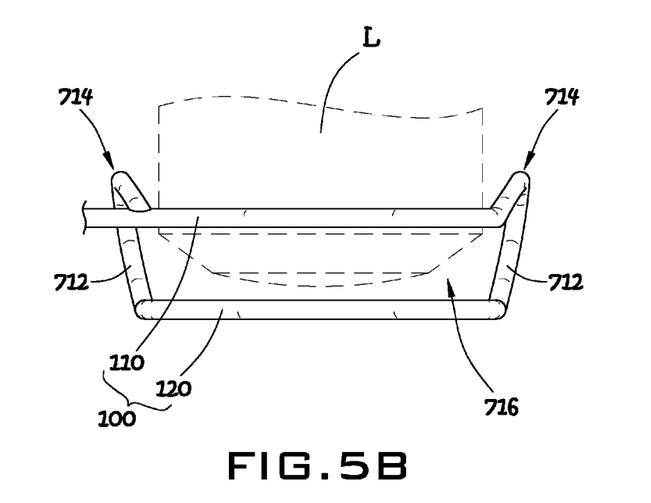

Referring now to FIGS. 5A and 5B, the modification of the probe guiding frame 700 is shown, wherein the probe guiders 710 are extended from the eyelid distensible frames 100 in an outward inclined manner. The probe guiding cavity 716 is formed to have in a conical configuration, wherein a cross sectional area of the probe guiding cavity 716 is gradually reducing from the peaks 714 of the probe guiders 710 above the upper distensible arms 110 to the lower distensible arms 120. In this modification, the curving arms 712 are slanted with respect to the eyelid distensible frames 100 to enlarge the opening size of the probe guiding cavity 716 within the peaks 714 of the probe guiders 710. Before the lens probe L is placed to contact with the cornea of the patient's eye, the lens probe L is easily disposed at the enlarged opening of the probe guiding cavity 716 within the peaks 714 of the probe guiders 710. Therefore, the lens probe L can be correctly disposed within the probe guiding cavity 716 to contact with the cornea of the patient's eye.

Figure 6A:
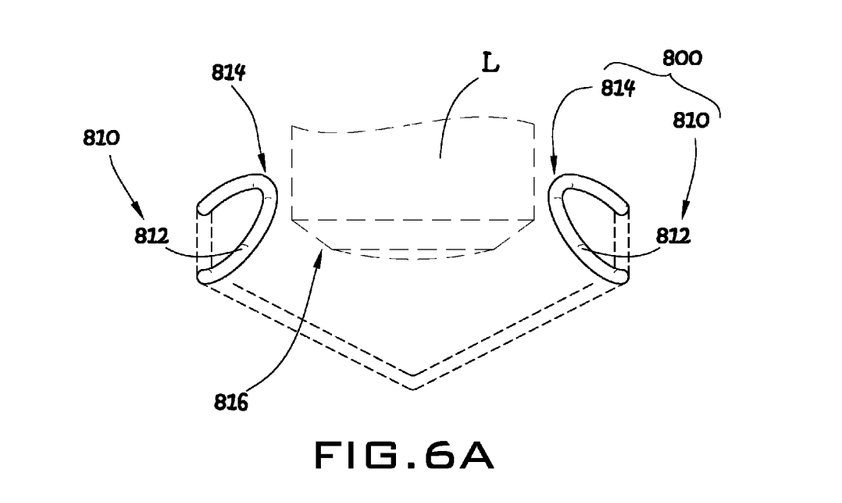
FIGS. 6A and 6B show the modification of the probe guiders extended from the eyelid distensible frames in an inward inclined manner according to the present invention.
Figure 6B:
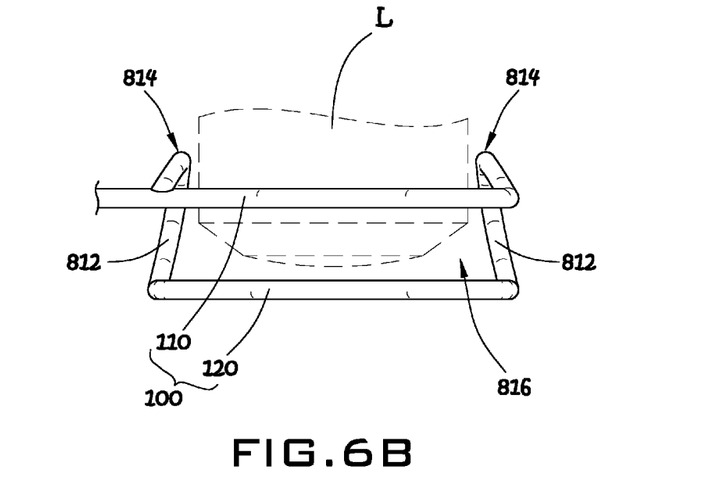

Referring now to FIGS. 6A and 6B, another modification of the probe guiding frame 800 is shown, wherein the probe guiders 810 are extended from the eyelid distensible frames 100 in an inward inclined manner. The probe guiding cavity 816 is formed to have in a conical configuration, wherein a cross sectional area of the probe guiding cavity 816 is gradually increasing from the peaks 814 of the probe guiders 810 above the upper distensible arms 110 to the lower distensible arms 120. In this modification, the curving arms 812 are slanted with respect to the eyelid distensible frames 100 to reduce the opening size of the probe guiding cavity 816 within the peaks 814 of the probe guiders 810. Therefore, when the lens probe L is disposed at the opening of the probe guiding cavity 816 within the peaks 814 of the probe guiders 810, the lens probe L is ensured to be correctly disposed within the probe guiding cavity 816 to contact with the cornea of the patient's eye.

Figure 7:
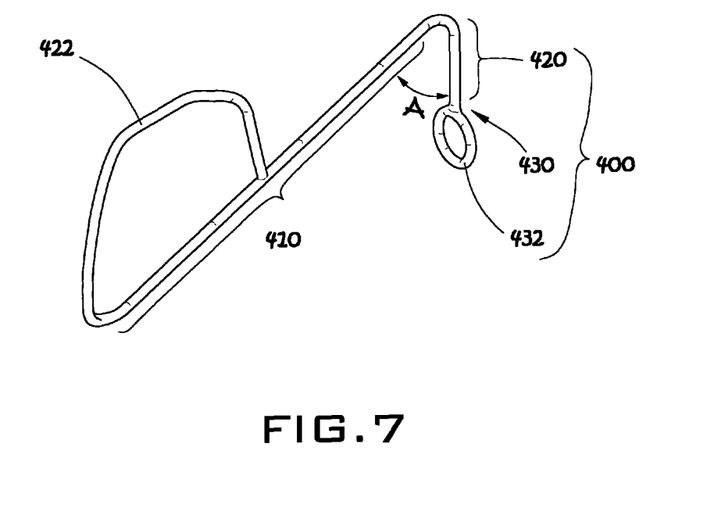
FIG. 7 is a top perspective view of an eye manipulator of the ophthalmic tool according to the present invention.

FIG. 7 depicts the eye manipulator for moving the eyeball of the patient to ensure the lens probe L to be aligned with the cornea of the patient after the eye of the patient is held opened by the ophthalmic speculum. Specifically, the eye manipulator of the present invention is able to move the eyeball of the patient when the lens probe L is placed to contact with the cornea of the patient's eye in an upright manner.

Referring now to FIG. 7, the eye manipulator has an angled arm 400 defining a handle portion 410 and a manipulating portion 420, and a manipulating end 430 formed at an end of the manipulating portion 420. An angle A between the handle portion 410 and the manipulating portion 420 of the angled arm 400 is an acute angle. It is preferred that the angle A between the handle portion 410 and the manipulating portion 420 is between 45° and 60°. The angled arm 400 defines a planar direction that the handle portion 410 and the manipulating portion 420 are aligned with the same planar direction.

The physician can hold the handle portion 410 to control the manipulating end 430 to be controllably contacted with a fornix area (fornix conjunctiva) to move the eyeball in an ergonomic manner when the lens probe L is positioned in an upright manner. In FIG. 7, the handle portion 410 of the angled arm 400 forms a finger loop 422 and the manipulating end 430 thereof forms a manipulating loop 432, wherein a planar direction of the manipulating loop of the manipulating end 430 is perpendicular to the planar direction of the manipulating portion 420 of the angled arm 400. The physician is able to hold the handle portion 420 by inserting the finger into the finger loop 422 to control the manipulating end 430. For example, the manipulating end 430 contacts the lower fornix area to move the eyeball downward.

According to this embodiment of the present invention, each of the ophthalmic speculum and the eye manipulator is constructed of a contiguous piece of wire. It is preferred that each of the ophthalmic speculum and the eye manipulator is made of shape-memory material.

According to this embodiment of the present invention, after the patient's eye is held open by the ophthalmic speculum of the present invention, the physician can use one hand to place the lens probe L within the probe guiding cavity 316 in an upright manner for capturing ophthalmic images and the other hand to hold the handle portion 410 of the eye manipulator for moving the eyeball so as to ensure the lens probe L to align with the cornea of the patient's eye.

While the embodiments and alternatives of the invention have been shown and described, it will be apparent to one skilled in the art that various other changes and modifications can be made without departing from the spirit and scope of the invention.

What is claimed is:

1. An ophthalmic tool for an eye imaging device having a lens probe to be directly contacted with a cornea of a patient's eye, wherein said ophthalmic tool comprises an ophthalmic speculum which comprises:
    two eyelid distensible frames adapted for engaging with an upper eyelid and a lower eyelid of the patient respectively, wherein each of said eyelid distensible frames comprises an upper distensible arm and a lower distensible arm for insertion under the patient's eyelid, wherein each of said upper distensible arms is a straight and elongated arm;
    a mechanism extended from said eyelid distensible frames to spread said eyelid distensible frames apart for holding the eye of the patient open; and
    a probe guiding frame which comprises four curving arms, upper ends of two of said curving arms being integrally extended from proximal ends of said upper distensible arm and said lower distensible arm respectively, upper ends of another two of said curving arms being integrally extended from distal ends of said upper distensible arm and said lower distensible arm respectively, wherein four peaks of said curving arms are formed at four turning points of said curving arms respectively and are served as four guiding points, wherein said peaks are located above said upper distensible arms so that said upper distensible arms are located between said peaks and said lower distensible arms, wherein a probe guiding cavity is formed within a space from said peaks to said lower distensible arms for guiding the lens probe to be disposed within said probe guiding cavity before and after the lens probe is aligned and contacted with the cornea of the patient's eye in a proper upright orientation.

2. The ophthalmic tool of claim 1 wherein each of said curving arms is curving up from said lower distensible arm to extend above said upper distensible arm and is then curving down to said upper distensible arm, so that said peak of said curving arm is located above said upper distensible arm.

3. The ophthalmic tool of claim 1 wherein said curving arms are outwardly and inclinedly extended from said lower distensible arms to said upper distensible arms to form said probe guiding cavity in a conical configuration, wherein a cross sectional area of said probe guiding cavity is gradually reducing from said peaks of said curving arms to said lower distensible arms.

4. The ophthalmic tool of claim 2 wherein said curving arms are outwardly and inclinedly extended from said lower distensible arms to said upper distensible arms to form said probe guiding cavity in a conical configuration, wherein a cross sectional area of said probe guiding cavity is gradually reducing from said peaks of said curving arms to said lower distensible arms.

5. The ophthalmic tool of claim 1 wherein said curving arms are inwardly and inclinedly extended from said lower distensible arms to said upper distensible arms to form said probe guiding cavity in a conical configuration, wherein a cross sectional area of said probe guiding cavity is gradually increasing from said peaks of said curving arms to said lower distensible arms.

6. The ophthalmic tool of claim 2 wherein said curving arms are inwardly and inclinedly extended from said lower distensible arms to said upper distensible arms to form said probe guiding cavity in a conical configuration, wherein a cross sectional area of said probe guiding cavity is gradually increasing from said peaks of said curving arms to said lower distensible arms.

7. The ophthalmic tool of claim 1 wherein said curving arms are extended from said lower distensible arms to said upper distensible arms in an upright manner to form said probe guiding cavity having a uniform cross sectional area from said peaks of said curving arms to said lower distensible arms.

8. The ophthalmic tool of claim 2 wherein said curving arms are extended from said lower distensible arms to said upper distensible arms in an upright manner to form said probe guiding cavity having a uniform cross sectional area from said peaks of said curving arms to said lower distensible arms.

9. The ophthalmic tool of claim 1 further comprising an eye manipulator for moving an eyeball of the patient to ensure the lens probe to be aligned with the cornea of the patient after the eye of the patient is held opened by said ophthalmic speculum, wherein said eye manipulator has an angled arm defining a handle portion and a manipulating portion, and a manipulating end formed at an end of said manipulating portion and formed a manipulating loop, wherein said handle portion is held and controlled to move said manipulating loop for contacting a lower fornix area to move the eyeball downward, wherein said handle portion of said angled arm forms a finger loop, wherein said angled arm defines a planar direction that said handle portion and said manipulating portion are aligned with the same planar direction, and a planar direction of said manipulating loop of said manipulating end is perpendicular to said planar direction of said manipulating portion of said angled arm.

10. The ophthalmic tool of claim 4 further comprising an eye manipulator for moving an eyeball of the patient to ensure the lens probe to be aligned with the cornea of the patient after the eye of the patient is held opened by said ophthalmic speculum, wherein said eye manipulator has an angled arm defining a handle portion and a manipulating portion, and a manipulating end formed at an end of said manipulating portion and formed a manipulating loop, wherein said handle portion is held and controlled to move said manipulating loop for contacting a lower fornix area to move the eyeball downward, wherein said handle portion of said angled arm forms a finger loop, wherein said angled arm defines a planar direction that said handle portion and said manipulating portion are aligned with the same planar direction, and a planar direction of said manipulating loop of said manipulating end is perpendicular to said planar direction of said manipulating portion of said angled arm.

11. The ophthalmic tool of claim 6 further comprising an eye manipulator for moving an eyeball of the patient to ensure the lens probe to be aligned with the cornea of the patient after the eye of the patient is held opened by said ophthalmic speculum, wherein said eye manipulator has an angled arm defining a handle portion and a manipulating portion, and a manipulating end formed at an end of said manipulating portion and formed a manipulating loop, wherein said handle portion is held and controlled to move said manipulating loop for contacting a lower fornix area to move the eyeball downward, wherein said handle portion of said angled arm forms a finger loop, wherein said angled arm defines a planar direction that said handle portion and said manipulating portion are aligned with the same planar direction, and a planar direction of said manipulating loop of said manipulating end is perpendicular to said planar direction of said manipulating portion of said angled arm.

12. The ophthalmic tool of claim 8 further comprising an eye manipulator for moving an eyeball of the patient to ensure the lens probe to be aligned with the cornea of the patient after the eye of the patient is held opened by said ophthalmic speculum, wherein said eye manipulator has an angled arm defining a handle portion and a manipulating portion, and a manipulating end formed at an end of said manipulating portion and formed a manipulating loop, wherein said handle portion is held and controlled to move said manipulating loop for contacting a lower fornix area to move the eyeball downward, wherein said handle portion of said angled arm forms a finger loop, wherein said angled arm defines a planar direction that said handle portion and said manipulating portion are aligned with the same planar direction, and a planar direction of said manipulating loop of said manipulating end is perpendicular to said planar direction of said manipulating portion of said angled arm.

13. The ophthalmic tool of claim 1 wherein said lower distensible arms are curved.

14. The ophthalmic tool of claim 4 wherein said lower distensible arms are curved.

15. The ophthalmic tool of claim 6 wherein said lower distensible arms are curved.

16. The ophthalmic tool of claim 8 wherein said lower distensible arms are curved.

17. The ophthalmic tool of claim 1 which is constructed of a contiguous piece of wire and is disposable, wherein said mechanism comprises a V-shaped wire spring integrally extended from said proximal ends of said upper distensible arms in an inclined manner to generate an expansion force along said upper distensible arms.

18. The ophthalmic tool of claim 4 which is constructed of a contiguous piece of wire and is disposable, wherein said mechanism comprises a V-shaped wire spring integrally extended from said proximal ends of said upper distensible arms in an inclined manner to generate an expansion force along said upper distensible arms.

19. The ophthalmic tool of claim 6 which is constructed of a contiguous piece of wire and is disposable, wherein said mechanism comprises a V-shaped wire spring integrally extended from said proximal ends of said upper distensible arms in an inclined manner to generate an expansion force along said upper distensible arms.

20. The ophthalmic tool of claim 8 which is constructed of a contiguous piece of wire and is disposable, wherein said mechanism comprises a V-shaped wire spring integrally extended from said proximal ends of said upper distensible arms in an inclined manner to generate an expansion force along said upper distensible arms.

* * * * *